United States Patent
Engqvist et al.

(10) Patent No.: US 7,699,925 B2
(45) Date of Patent: Apr. 20, 2010

(54) SYSTEM FOR A DENTAL FILLING MATERIAL OR IMPLANT MATERIAL, AND POWDERED MATERIAL, HYDRATION LIQUID, IMPLANT MATERIAL AND METHOD OF ACHIEVING BONDING

(75) Inventors: Håkan Engqvist, Knivsta (SE); Leif Hermansson, Lanna (SE); Nils-Otto Ahnfelt, Uppsala (SE); Jesper Loof, Uppsala (SE); Lars Kraft, Uppsala (SE); Jan-Erik Schulz-Walz, Hamburg (DE)

(73) Assignee: Doxa AB, Uppsala (SE)

( * ) Notice: Subject to any disclaimer, the term of this patent is extended or adjusted under 35 U.S.C. 154(b) by 627 days.

(21) Appl. No.: 10/518,084

(22) PCT Filed: Jun. 11, 2003

(86) PCT No.: PCT/SE03/00954

§ 371 (c)(1),
(2), (4) Date: Aug. 24, 2005

(87) PCT Pub. No.: WO04/000239

PCT Pub. Date: Dec. 31, 2003

(65) Prior Publication Data

US 2006/0086287 A1    Apr. 27, 2006

(30) Foreign Application Priority Data

Jun. 20, 2002 (SE) ................................. 0201920
Jun. 20, 2002 (SE) ................................. 0201921
Oct. 9, 2002 (SE) ................................. 0202998

(51) Int. Cl.
  *A61K 6/06* (2006.01)
  *C04B 28/06* (2006.01)

(52) U.S. Cl. ............... 106/35; 106/690; 106/691; 106/692; 106/695; 623/23.62; 433/228.1

(58) Field of Classification Search ............ 106/35, 106/690, 691, 692, 695; 623/23.62; 433/228.1
See application file for complete search history.

(56) References Cited

U.S. PATENT DOCUMENTS

| 3,873,327 | A |  | 3/1975 | Duff |  |
|---|---|---|---|---|---|
| 4,518,430 | A |  | 5/1985 | Brown |  |
| RE33,221 | E | * | 5/1990 | Brown et al. | 423/308 |
| 4,959,104 | A | * | 9/1990 | Iino et al. | 106/691 |
| 5,281,265 | A |  | 1/1994 | Liu |  |
| 5,342,441 | A | * | 8/1994 | Mandai et al. | 106/35 |
| 5,525,148 | A | * | 6/1996 | Chow et al. | 106/35 |
| 6,143,069 | A | * | 11/2000 | Brothers et al. | 106/678 |
| 6,521,264 | B1 |  | 2/2003 | Lacout |  |

FOREIGN PATENT DOCUMENTS

| CA | 2 027 833 C | 4/2003 |
|---|---|---|
| DE | 4303575 | 4/1994 |
| JP | 59-111753 A | 6/1984 |
| JP | 59-214443 A | 12/1984 |
| JP | 62-201825 A | 9/1987 |
| JP | 3-170157 A | 7/1991 |
| JP | 7-194686 A | 8/1995 |
| WO | 9402411 | 2/1994 |
| WO | WO 97/00591 A1 | 1/1997 |
| WO | 9926673 | 6/1999 |
| WO | 9945979 | 9/1999 |
| WO | 9948809 | 9/1999 |
| WO | WO 00/21489 A1 | 4/2000 |
| WO | 02053068 | 7/2002 |

OTHER PUBLICATIONS

Technical Data Sheet for Refcon, Aug. 2007.*
co-pending European Application 03 733 717.7, Office Action dated Apr. 2, 2009.
Japanese Office Action dated Feb. 24, 2009.

* cited by examiner

Primary Examiner—C. Melissa Koslow
(74) Attorney, Agent, or Firm—Young & Thompson

(57) ABSTRACT

A system for a dental filling material or an implant material, alternatively a system for bonding between a tooth or a bone and a dental filling material and a implant material, respectively, which system comprises a water based hydration liquid and a powdered material, the binder phase of which powdered material essentially consisting of a calcium based cement system, which powdered material has the capacity following saturation with the liquid reacting with the binder phase to hydrate to a chemically bonded ceramic material. According to the invention, said powdered material and/or said hydration liquid comprises water soluble phosphate or a phase that has the capacity to form water soluble phosphate, whereby the system exhibits the capacity during hydration to form apatite. The invention also relates to the powdered material and the hydration liquid as such, an implant material and a method of achieving bonding.

20 Claims, 2 Drawing Sheets

SYSTEM FOR A DENTAL FILLING MATERIAL OR IMPLANT MATERIAL, AND POWDERED MATERIAL, HYDRATION LIQUID, IMPLANT MATERIAL AND METHOD OF ACHIEVING BONDING

TECHNICAL FIELD

The present invention relates to a system for a dental filling material or an implant material, alternatively a system for bonding between a tooth or a bone and a dental filling material and a implant material, respectively, which system comprises a water based hydration liquid and a powdered material, the binder phase of which powdered material essentially consisting of a calcium based cement system, which powdered material has the capacity following saturation with the liquid reacting with the binder phase to hydrate to a chemically bonded ceramic material. The invention also relates to the powdered material and the hydration liquid as such, and also an implant material and a method of achieving bonding.

In the following, the terms "system", "cement system", "binding agent system" and "binder system" and similar relate to both embodiments of the invention mentioned above, i.e. the system for a dental filling material or implant material and the system for bonding between a tooth or a bone and a dental filling material and an implant material, respectively, if nothing else is said.

The term "implant" or "implant material" and similar, also comprise orthopaedic bone void fillers.

PRIOR ART

The present invention relates to binding agent systems of the hydrating cement system type, in particular cement-based systems that comprise chemically bonded ceramics in the group that consists of aluminates, silicates, phosphates, sulphates and combinations thereof, having calcium as the major cation. The invention has been especially developed for biomaterials for dental and orthopaedic applications, such as implants including fillers and coatings and bonding systems.

For materials, such as dental filling materials and implants, that are to interact with the human body, it is an advantage that the materials are made as bioactive or biocompatible as possible. As to ceramic materials, it can be said that apatite is the body's own ceramic, why apatite from this point of view ought to be excellent as a dental filling material or implant. Apatite materials as such however generally don't exhibit the other properties that are required for dental filling materials and implants, such as good handling ability with simple applicability in a cavity, moulding that permits good modellability, hardening/solidification that is sufficiently rapid for filling work and provides serviceability directly following a visit to the dentist, high hardness, corrosion resistance, good aesthetics and good long time properties in terms of dimensional stability. For the purpose of providing a material that fulfils at least most of these required properties, a material has been developed according to what is presented in SE 463,493, SE 502,987, WO 00/21489, WO 01/76534 and WO 01/6535, e.g. It is also suggested in SE 463,493 and SE 502,987 that such materials may comprise an apatite ballast.

When a dental filling/implant material is applied against tooth or a bone, it is furthermore of utmost importance that a good bonding is achieved between the material and the tooth/bone. Known dental filling materials according to the patent applications mentioned above will certainly give an acceptable bonding, but there is free scope for improvements.

ACCOUNT OF THE INVENTION

The present invention aims at providing a system for the production of a chemically bonded ceramic material of a powdered material, the binder phase of which essentially consisting of a calcium based cement system, which system has the capacity to form apatite in-situ. By capacity to form apatite in-situ it is hereby meant that the system comprises the components that are necessary for the formation of apatite, hydroxyapatite or fluoride-apatite ($(Ca_5(PO_4)_3OH$ and $Ca_5(PO_4)_3F$, respectively) for example, and optionally some other biologically favourable phase, and that the system allows for such phases to be formed during and/or after the hydration reaction. Hereby, the advantage is at least attained that apatite need not be added as a separate additive. The material formed can be said to constitute a chemically bonded ceramic composite that exhibits many advantages as a dental filling material, as implant material (comprising fillers) or as a coating layer on an implant material, or as a bonding material. The formation of apatite in the material is a sign of the material being bioactive and co-operating with the body. Furthermore, the distribution of apatite will be homogeneous in the material, also in contact zones against biological material, bone and tooth tissue. The formation of apatite in such contact zones is especially favourable for the binding or the bonding alternatively. Another advantage for the formation of apatite is that the environment is basic. Since apatite is an endogenous substance, the binder system will result in excellent binding properties with a very tight union between the dental filing/implant material and the tooth/bone. The integration with the surroundings having a content of apatite is very important, especially for dental filling materials, orthopaedic pastes and materials lying as a coating on implants. The latter relates to in-situ prepared surface coatings of a chemically bonded ceramic composite based on apatite, having a great influence on bone integration.

Surprisingly, it has been found that a calcium based cement system comprising phosphate, at a boundary or a gap between a tooth or a bone and a dental filling material and an implant material, respectively, not only provides for the formation of a chemically bonded ceramic composite comprising apatite, but also leads to a faster healing of the tooth or the bone. It has been found that a chemical and biological integration takes place, that leads to an additional surface growth that chemically diminishes the gap between the tooth/bone and the dental filling material/implant material, but that also, due to the presence of apatite, will result in a faster biological sealing of the gap. The healing or growing process of the bone or the tooth is favoured by the supply of calcium and phosphorous from the cement system.

Accordingly, calcium is taken from the calcium based cement system, a calcium aluminate system e.g. Below a surface layer of formed apatite, the content of Ca will therefore be somewhat reduced, which leads to an increased formation of gibbsite phase in the produced ceramic material. The extension of this gibbsite phase may be controlled by the content of Ca and the addition of phosphate in the contact zone.

Another aspect of the formation of hydroxyapatite (formation of HAP) in connection with the general mechanism at hardening comprising dissolving and depositing, is that the system may act to favour healing at attacks on tooth or bone tissue. Hereby, the biological material that has lost its hard material (its biologically formed apatite) is remineralised by Ca-aluminate with a source of phosphorous reacting with water of body fluid. The material is dissolved, i.e. becomes a solution and ions such as calcium, aluminate, phosphate, hydroxyl and optional additives, such as fluoride, is deposited in all voids, including those coming from previous bone decay. This means that also caries that unintentionally has been left after treatment, can be remineralised. Also other bone materials can be favoured in healing in a corresponding manner, e.g. related to osteoporosis etc.

At attacks of caries or other bone decay, the surface may therefore be pre-treated by a cement system that contains a lot of calcium and phosphorous, in order to facilitate a fast and efficient formation of materials containing HAP. One concept is that the hydration liquid contains phosphoric acid with tricalcium phosphate and that the binder phase of the cement essentially consists of fine grain (<5 µm, preferably <1 µm grain size) of $C_3A$ (i.e. $3CaO.Al_2O_3$) and/or $C_3S$ (i.e. $3CaO.SiO_2$) and/or $C_2S$ (i.e. $2CaO.SiO_2$).

As to the coating of implants, the integration with the bone may be improved and accelerated by:

1. HAP being brought to constitute a part of a coating of CAH-HAP on an implant of metal, ceramics or polymer. The coating being produced and hydrated before implantation.
2. Accelerated/increased formation of HAP after implantation, by an outermost layer having been applied onto the coating by extra addition of non-reacted CA+phosphate. The surface layer may contain a source of phosphorous or the surface may be steeped in a phosphate-containing aqueous solution. Effect: Additional surface growth chemically diminishes the gap, and a faster biological sealing of the gap takes place due to presence of HAP. See also the drawings description.

Another way of achieving non-reacted material in the outermost part of the coating, is to:

3. Apply a torque on the coating just before or in connection with the implantation. The surface layer may contain a source of phosphorous or the surface may be steeped in a phosphate-containing aqueous solution.

Effect: Releases non-reacted material
CAH=the calcium aluminate system
CA=calcium aluminate, raw material without water/hydration liquid
HAP=hydroxyapatite In the following, an explanation is given considering the effect of the basic system on spontaneous formation of HAP in boundaries between bone tissue and added CA. (Of course, the mechanism also applies generally at presence of phosphate.) At a variation of pH in its surroundings, hydrogen phosphate and dihydrogen phosphate (included in the buffering system of the body) will want to contribute to a neutralisation. A basic system is obtained if CA material is present. The buffering system tries to take care of surplus hydroxyl ions, to form water by a shifting in the buffering system from the dihydrogen phosphate to the hydrogen phosphate or to a phosphate ion (an ion without hydrogen, one hydrogen ion is released and forms water together with a hydroxyl ion). As the equilibrium is shifted towards phosphate, the phosphate content of the solution is increased and apatite=calcium phosphate hydroxide=$Ca_5(PO_4)_3(OH)$ is formed together with Ca-ions and hydroxyl ions. Apatite has a low solubility product, which favours the deposition of the apatite in the surrounding system having a surplus of Ca, hydroxyl ions and the tendency to shift the buffering system towards phosphate.

According to the invention, a system is accordingly presented for a dental filling material or an implant material, a bonding system for a dental filling material or an implant material, a powdered material, a hydration liquid and an implant material and a method of achieving bonding, according to the enclosed claims.

The Powdered Material

The powdered material consists of a calcium based, basic ceramic powder of aluminates, silicates, phosphates, sulphates and combinations thereof, preferably aluminates. According to the invention, the powdered material comprises water soluble phosphate or a phase that forms phosphate ions during hydration, whereby the cement system exhibits the capacity during hydration to form apatite.

In addition:

a. Said water soluble phosphate may consist of a water soluble, phosphate containing phase, alkali phosphates e.g. For the bonding system especially, the content of phosphate is suitably high, preferably 1-90%, more preferred 5-60% and even more preferred 10-30%. Effect: an increase of the phosphate content in the material will result in an increased content of apatite (not only limited to the phosphate content of the solution).

b. The material may comprise grains of phosphate-containing phase, preferably hydroxyapatite and fluoride-apatite, Effect: controlling the precipitation of apatite.

c. The material may comprise additives of collagen, elastin or other high-molecular proteins that are coated in-situ or are pre-coated by apatite from a saturated solution. Effect: to control the deposition of apatite.

d. The material may comprise an additive of a fluoride-containing phase of non difficultly soluble character, fluoride-containing glass (glass ionomer glass) e.g. of non difficultly soluble character, at contents below 10%. Other examples of fluoride-containing phase are calcium fluoride ($CaF_2$) or sodium fluoride (NaF). Effect: a way of introducing fluoride in the material, whereby fluoride-apatite can be formed.

e. In the bonding system, the binder phase suitably has a larger mole content of calcium that of aluminium, in which case the binder phase preferably comprises or essentially consists of $3CaO.Al_2O_3$ (C3A). Accordingly, the ceramic powder is preferably modified for an increased Ca-content in aluminate (the $C_3A$-CA-system). If using C3A or some other phase that is rich in calcium, more calcium is obtained that can react with phosphorous to form apatite. In addition, C3A hardens fast which is good in a thin layer that is to be applied onto the tooth/bone before the filing takes place.

f. The material may comprise carbonate or biologically existing ions that may form: oxalates, lactates, calcite, aragonite. That is, the carbonate or boilogically existing ions has the capacity to form calcite and/or aragonite oxalates, lactates, citrates. Carbonate ions may for example form calcite and calcium may form difficultly soluble biological salts with the anion of the lactic acid, lactate etc.

Effect: by controlling the concentration and the composition of the ions, different biological phases containing Ca may be deposited. This also applies to water-soluble additives in the powder raw material.

g. The addition of water-soluble phosphate may be achieved by addition of a phase that forms phosphate ions during hydration ($P_2O_5$, active glass containing phosphorous, bioglass, Apatite-Wollastonite glass e.g.). Additives of elements that deliver phosphate in water, such as tricalcium phosphate, alkali salts, are also included in the concept of "addition of water-soluble phosphate".

h. It is also possible to supply phosphorous by pre-coating particles (filler or cement) with phosphate or phosphorous. Such a pre-coating may easily be performed by dissolving crystals of phosphoric acid e.g. in an inert solvent, isopropanol e.g. Fillers and cement particles are then mixed in the isopropanol, where after the isopropanol is driven off and phosphate/phosphorous remains on the particles.

i. It is also possible to form solid solutions of cement phase (calcium silicates or calcium aluminates) and phosphorous, according to the principles described in SE-A0-0103189-7. The concentration of phosphorous that is possible to dissolve in the cement is <10% by atoms, preferably <5% by atoms.

j. Also other apatites than hydroxyapatite and that function well in the body, can be included in the concept of "apatite" and may in the present text also be included in the concept of "hydroxyapatite", chloride-apatite, carbonate apatite, fluoride-apatite and magnesium apatite e.g. Chloride-apatite may easily be formed by dissolving chloride in the hydration liquid or alternatively by incorporating a readily soluble salt in the material. Carbonate apatite may be formed by hydrating in carbonated phosphoric acid. Fluoride-apatite may be formed by addition of fluoride, in the form of LiF e.g. as an accelerator and magnesium apatite may be formed by precipitation reaction at the forming of apatite with Mg in the aqueous solution.

k. For dental filling or implant materials, the powdered material may take the form of a raw compact that preferably exhibits a degree of compaction of at least 55% by volume solid phase, more preferred at least 60% by volume solid phase, even more preferred at least 65% by volume solid phase and most preferred of all at least 70% by volume solid phase.

l. As an alternative, the powdered material may exist in loose powder form, in which case it is mixed with the hydration liquid to form a suspension that is subsequently drained and compacted.

It is especially preferred that the main binder phase of the cement system consists of calcium aluminate (Ca-aluminate), since:

1. Ca-aluminates will give a basic local environment for the apatite, which makes that phase stable (no dissolution, preventing formation of plaque and lactic acid).
2. Ca-aluminate exists in surplus and is formed in all pores in the material—contributes to fill the material—if only apatite was used, too little water would be transformed in order for water-filled porosity to be filled by hydrate.
3. Ca-aluminate is deposited by acid-base reaction, in which water reacts with the powdered material, that starts to dissolve. In the solution, all constituents exist that are needed for the formation of both calcium aluminate hydrate, gibbsite and apatite (if some type of phosphorous is supplied) and possibly some other biologically favourable phase (calcite, aragonite, lactate etc.). When the solubility product of each substance is reached, a deposition starts to take place. The deposition takes place everywhere, including inside the microspaces between the filling material and the tooth wall. Small crystals are deposited in the surface topography in the tooth wall or some other biological contact surface and contributes to the complete disappearance of the contact zone of filling material-tooth/bone, leading to micro-structural integration. No gap can be discovered in magnifications of up to 20,000 times.

Concludingly: Ca-aluminate is advantageous at presence of apatite, in order to a. Protect the apatite from chemical dissolution at a low pH, b. Ensure that a dense product exists/is formed. (The pump in the system is Ca ions, aluminate ions and OH ions). Additionally added ions such as phosphates, fluorides, carbonates etc. will give a secondary, complementing, purely biological phase, c. Contribute to the formation of a completely tight contact zone (micro-structural integration).

The Hydration Liquid

The hydration liquid consists of an aqueous liquid that according to the invention comprises water soluble phosphate or a phase that forms phosphate ions during hydration, whereby the cement system exhibits the capacity during hydration to form apatite. The water soluble phosphate comprises phosphate ions in the group that consists of $PO_4^{3-}$, $HPO_4^{2-}$, $H_2PO_4^-$, and other phosphorous-containing ions, or the water soluble phosphate is hydro-ammonium phosphate.

In addition:

a) Said water soluble phosphate forms phosphate ions in the liquid, preferably $PO_4^{3-}$, $HPO_4^{2-}$, $H_2PO_4^-$ or some other phosphorous-containing ion.

b) The liquid may also be a bonding liquid, that is applied on bone or tooth before the dental fling material/implant material with additional (free from phosphate or phosphate-containing) hydration liquid is applied, in which case water soluble phosphate in the bonding liquid forms apatite with the dental filling material/implant material.

c) The liquid may comprise carbonate or biologically existing ions that may form: oxalates, lactates, calcite, aragonite. That is, the carbonate or biologically existing ions has the capacity to form calcite and/or aragonite, oxalates, lactates, citrates. Carbonate ions may for example form calcite and calcium may form difficultly soluble biological salts with the anion of the lactic acid, lactate etc. Effect: by controlling the concentration and the composition of the ions, different biological phases containing Ca may be deposited.

d) The concentration of phosphate ions should be 0.01-5 M, preferably 0.1-2 M and most preferred 0.5-1.5 M. Specifically for the bonding system, the preferred concentrations are even higher, namely 0.01-5 M, preferably 0.5-4 M, most preferred 1-3 M. Suitably, phosphate ions exist in concentrations close to saturation in the bonding liquid or the liquid for the bonding system. By using very high concentrations, an increased deposition of apatite may be obtained in the zone between the tooth/bone and the material. Effect: A high concentration will give more apatite phase.

e) The hydration liquid pH should be adjusted to at least 7, preferably 7-12.5 and even more preferred 7-11, preferably by use of a buffering system of phosphates or carbonates, e.g.

Effect: The pH controls the equilibrium for deposition of apatite and katoite (main phase in the Ca-aluminate-hydrate system). Accordingly, the system pH is also at least 7, preferably 7-12.5 and even more preferred 7-11, preferably by use of a buffering system of phosphates or carbonates e.g.

f) The liquid may comprise added fluoride ions, to a concentration of fluoride ions in the range of 0.01-5 M, preferably 0.1-2 M, most preferred 0.5-1 M, Effect: gives a formation of fluoride-apatite, together with katoite. (Fluoride-apatite is even more stable than hydroxyapatite).

g) The liquid may comprise a suspended or emulsified, non hydrated or partially hydrated calcium aluminate cement, for the formation of a basic environment for the apatite.

h) The liquid may comprise accelerator and/or superplasticizer.

i) Chloride-apatite may be formed by dissolving chlorine in the hydration liquid. Carbonate apatite may be formed by hydrating in carbonated phosphoric acid. Fluoride-apatite may be formed by addition of fluoride, in the form of LiF e.g. as an accelerator and magnesium apatite may be formed by precipitation reaction at the forming of apatite with Mg in the aqueous solution.

The Application Method for Bonding Systems

Before the bonding system is applied on the tooth wall/the bone, the tooth wall/the bone should be prepared by so called coarsening technique, that normally is performed by etching and/or mechanical coarsening techniques, micro-blasting e.g. Different suitable, highly concentrated etching agents can be used, but most preferably phosphate-containing etching agents are used, preferably an etching agent in the group that consists of phosphoric acid, hydrophosphoric acid, phosphate buffer and citrates, that will give remaining phosphate substances on the surface that is being treated. After the coarsening, the hydration liquid and the powdered material for the bonding system are mixed and the bonding system thus formed is applied as a thin layer on the tooth/bone, preferably by spraying or painting. Thereafter, the tooth is ready to be filled by the dental filing material or the implant material to be applied/attached to the bone.

It is however also conceivable, instead of a bonding system according to what has just been described, or in combination therewith, to prepare the tooth wall/bone (by spraying or painting e.g.) with a bonding liquid which in that case constitutes one embodiment of a hydration liquid according to the invention and that also may constitute an etching agent. Such a bonding liquid/hydration liquid may accordingly exhibit the features described above in connection with the hydration liquid and may solely supply the system with enough water soluble phosphate for a strongly enhanced bonding. Of course, additional phosphate for the formation or apatite may be supplied via the dental filling material/implant material/bonding material, if desired. It should also be understood that such a bonding liquid may be allowed completely or partially to dry up, in which case its dissolved contents (comprising phosphate substances) completely or partially will deposit on the tooth/bone, in order then to be re-dissolved as the dental filling material/implant material with additional (free from phosphate or phosphate-containing) hydration liquid is applied thereupon.

The Dental Filling or Implant Material in Connection with Bonding Systems

It is preferred for an extra good bonding to the tooth/bone, that the dental filling material/implant material consists of a chemically bonded ceramic material that is compatible with the bonding system. Accordingly, it is preferred that also the dental filling material/implant material comprises a powdered material, the binder phase of which essentially consisting of a calcium based cement system, which powdered material has the capacity following saturation with a hydration liquid reacting with the binder phase to hydrate to a chemically bonded ceramic material, said powdered material and/or said hydration liquid comprising water soluble phosphate or a phase that forms phosphate ions during hydration, whereby the dental filling material/implant material exhibits the capacity during hydration to form apatite. Hereby, an excellent integration and bonding is achieved between the actual bonding system and the dental filling material/implant material. It should be understood that also other aspects that have been described here for the bonding system, can be applicable for the dental filling material/implant material. However, the dental filling material/implant material is suitably adapted for the formation of a lower content of apatite, 0.01-30% by volume apatite preferably being formed in the cement system during the hydration. The bonding system has the capacity during hydration to form 0.01-60% by volume in the system.

DESCRIPTION OF DRAWINGS

In the following, the mechanism at implanting will be described in greater detail with reference to a preferred embodiment. A photograph of micro-structural integration when using a bonding system according to the invention, is also shown.

In the figures, detail no. 1 symbolises an implant with a metal, ceramic or polymeric substrate. FIG. 1 shows how a coating layer 2 of CAH-HAP has been applied and hydrated. FIG. 2 shows how an extra, outermost layer 3 has been applied on the coating 2, just before the implantation is to begin. The coating layer 2 suitably exhibits a thickness of 0.5-20 µm, preferably less than 10 µm, and even more preferred 0.5-3 µm. The outer layer 3 suitably exhibits a thickness of 0.5-10 µm, preferably less than 5 µm, and even more preferred 0.5-3 µm. The outer layer 3 is composed of non-reacted CA (without any hydration liquid) that comprises phosphate. The size of the crystals in the phases in layer 2 and/or 3 is 5 µm at the most, preferably less than 1 µm.

FIG. 3 shows how the implant 1 with the coating layer 2 and the outer layer 3 has been implanted against a biological wall in existing hard tissue, usually bone tissue 4, of the patient. Immediately after the implantation, there is a gap x of 10 µm magnitude between the outer surface of the implant and the hard tissue, which gap always will arise even if the implant is put completely in abutment with the hard tissue.

FIG. 5 shows how the implant 1 has been integrated with the hard tissue 4, after healing 4'. The healing and integration will be extra fast, since Ca-ions and phosphate/apatite are supplied to the area via the coating 2 and the outer layer 3. The biologically induced growth of new bone tissue 4' is united with the outer grown layer 3'. The biologically related growth is positively affected by the presence of HAP. The size of the gap has, according to the above, been diminished by the chemical growth of layer 3', which per se will accelerate the biological filling of new bone tissue 4' in the gap.

FIG. 6 shows a photograph in 20,000 times magnification, of the transition area between a tooth wall and a dental filling material, in which transition area a bonding system according to the invention has been applied. The photograph shows a formation of a tight union between filling and tooth wall by deposition/application of a chemically bonded ceramic composite in the bonding system. This depositing takes place everywhere internally in the pore system of the bonding system but also in micro-spaces between the filling material and the tooth wall. Small crystals are deposited in the surface topography and will, by micro-structural integration, contribute to the complete disappearance of the contact zone between filling material-tooth.

Figure 1:
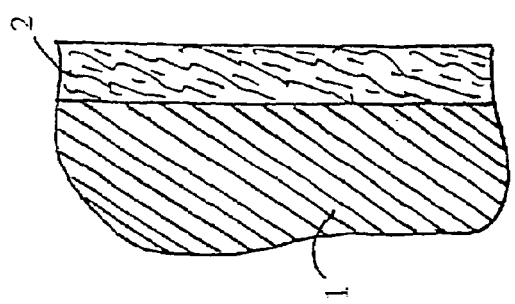
FIG. 1 shows an outer part of an implant with a coating, as seen in cross-section.
Figure 2:
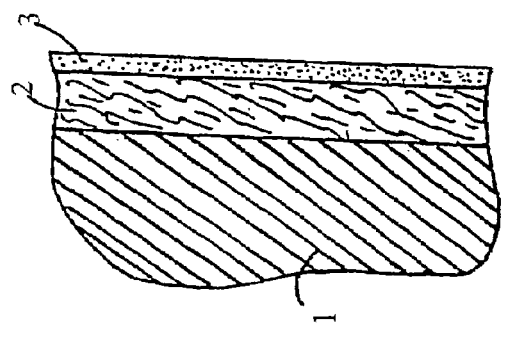
FIG. 2 shows the part according to FIG. 1, provided with an extra, outermost layer, as seen in cross-section.
Figure 3:
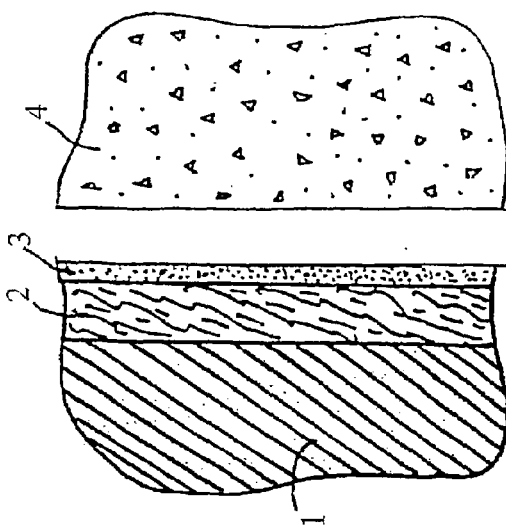
FIG. 3 shows the part according to FIG. 2 immediately after it has been implanted against a biological wall, as seen in cross-section, FIG. 4 show the system according to FIG. 3, after about one hour.
Figure 4:
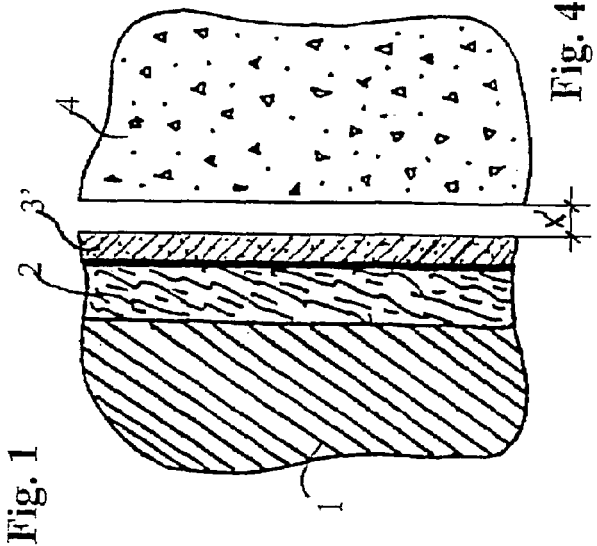
FIG. 4 shows how the gap, after about one hour, has shrunk to a gap x' of about 7 µm. This depends on the outer, non-reacted layer 3 having hydrated to a hydrated layer 3', in which case 1-3 µm surface growth normally has occurred by chemical mass growth on the outer layer 3, 3'. This mass growth depends on an uptake of water, body fluid or hydration liquid, in the non-reacted layer 3.
Figure 5:
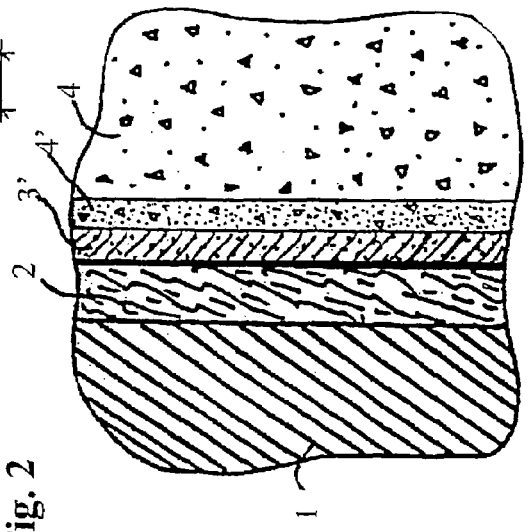
FIG. 5 shows the system according to FIG. 3-4 after healing.
Figure 6:
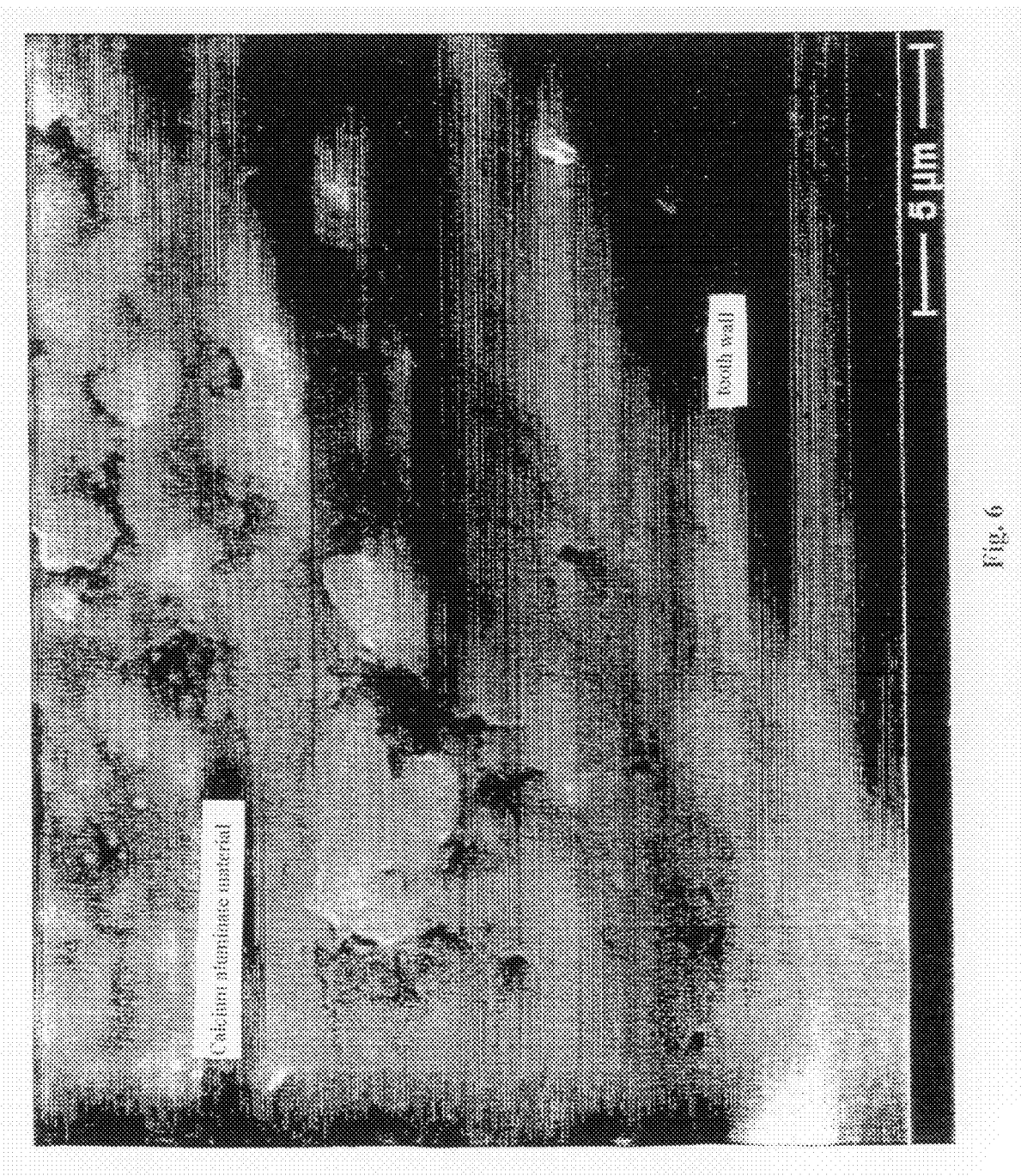
FIG. 6 shows a photograph in 20,000 times magnification, of the transition area between a tooth wall and a dental filling material, in which transition area a bonding system according to the invention has been applied.

The invention is not limited by the preferred embodiments but may be varied within the scope of the claims. In particular, it should be realised that other aspects of the system/powdered material/hydration liquid may follow what is taught in SE 463,493, SE 502,987, WO 00/21489, WO 01/76534, WO 01/76535, SE-A0-0103189-7 or SE-A0-0103190-5, which aspects hereby are incorporated by reference. It should also be understood that the powdered material and the hydration liquid, respectively, may be used in combination but also separately and in that case together with conventional hydration liquids and powdered materials, as for example those described in the just mentioned older patent applications.

The invention claimed is:

1. A system for a dental filling material or an implant material, alternatively a system for bonding between a tooth or a bone and a dental filling material and an implant material, respectively, comprising:
   a water based hydration liquid; and
   a powdered material, wherein,
   said system has a pH of at least 7,
   said powdered material comprises a binder phase that essentially consists of a calcium aluminate based cement system,
   said calcium aluminate based cement system has a larger mole content of calcium than of aluminium,
   said hydration liquid reacts with the binder phase to form a chemically bonded ceramic material upon saturation of said powdered material with said hydration liquid, and
   at least one of said powdered material and said hydration liquid comprises water soluble phosphate or a phase that forms phosphate ions during hydration so that the system has the capacity to form apatite during hydration of said powdered material.

2. The system according to claim 1, wherein the system has the capacity to form, during hydration, 0.01-30% by volume apatite in the system.

3. The system according to claim 1, wherein the system is a bonding system that has the capacity to form, during hydration, 0.01-60% by volume apatite in the system.

4. The system according to claim 1, wherein,
   the binder phase essentially consists of a fine grain of $3CaO \cdot Al_2O_3$ having a mean particle size of less than 5 μm, and
   the hydration liquid comprises phosphoric acid with tricalcium phosphate.

5. The system according to claim 1, wherein, said calcium aluminate based cement system further comprises at least one of aluminates, silicates, phosphates, and sulphates.

6. The system according to claim 1, wherein, said water soluble phosphate is an alkali phosphate.

7. The system according to claim 1, wherein, said powder material has a degree of compaction of at least 55% by volume solid phase.

8. The system according to claim 1, wherein, said hydration liquid has a pH of at least 7.

9. The system according to claim 1, wherein, said hydration liquid comprises at least one of an accelerator and a superplasticizer.

10. The system according to claim 1, wherein, the powdered material comprises the water soluble phosphate or the phase that forms phosphate ions during hydration.

11. The system according to claim 10, wherein, said powder material comprises high-molecular proteins.

12. The system according to claim 10, wherein, said powder material comprises from 0.5% and less than 10% of a fluoride-containing phase of non difficultly soluble character.

13. The system according to claim 10, wherein, said powder material comprises carbonate or biologically existing ions that have the capacity to form at least one salt selected from the group consisting of calcite, aragonite, oxalates, lactates, and citrates.

14. The system according to claim 10, wherein, the phosphate or phosphate ion-forming phase exists as particles that are precoated by a material comprising phosphate or phosphate-containing phase.

15. The system according to claim 10, wherein, the phosphate or phosphate ion forming phase exists by the cement system comprising phosphate-containing phase in solid solution in the cement system.

16. The system according to claim 1, wherein,
   the hydration liquid comprises water soluble phosphate or a phase that forms phosphate ions during hydration.

17. The system according to claim 16, wherein, said water soluble phosphate comprises phosphate ions selected from the group consisting of $PO_4^{3-}$, $HPO_4^{2-}$, $H_2PO_4^-$, and other phosphorous-containing ions, or said water soluble phosphate is hydro-ammonium phosphate.

18. The system according to claim 16, wherein, said hydration liquid comprises suspended or emulsified, non hydrated or partially hydrated calcium aluminate cement, for the formation of a basic environment for the apatite.

19. The system according to claim 16, wherein, said hydration liquid comprises carbonate or biologically existing ions that has the capacity to form at least one salt selected from the group consisting of calcite, aragonite, oxalates, lactates, and citrates.

20. The system according to claim 16, wherein, said hydration liquid comprises fluoride ions at a concentration of 0.01-5 M.

* * * * *